United States Patent
Li et al.

(10) Patent No.: US 11,937,604 B2
(45) Date of Patent: Mar. 26, 2024

(54) PIGM GENE RELATED TO NILAPARVATA LUGENS (STÅL) REPRODUCTION AND APPLICATION THEREOF

(71) Applicant: China Jiliang University, Hangzhou (CN)

(72) Inventors: Yabin Li, Hangzhou (CN); Ronger Zheng, Hangzhou (CN); Yipeng Xu, Hangzhou (CN); Xiaoping Yu, Hangzhou (CN)

( * ) Notice: Subject to any disclaimer, the term of this patent is extended or adjusted under 35 U.S.C. 154(b) by 0 days.

(21) Appl. No.: 17/474,028

(22) Filed: Sep. 13, 2021

(65) Prior Publication Data

US 2023/0079787 A1    Mar. 16, 2023

(51) Int. Cl.
*C12N 15/11*      (2006.01)
*A01N 63/10*      (2020.01)
*C07K 14/325*    (2006.01)

(52) U.S. Cl.
CPC ............ *A01N 63/10* (2020.01); *C07K 14/325* (2013.01); *C12N 15/11* (2013.01)

(58) Field of Classification Search
CPC ..................................................... C12N 15/11
See application file for complete search history.

*Primary Examiner* — Ekaterina Poliakova-Georgantas

(57) ABSTRACT

A nucleotide sequence is shown in SEQ ID NO.1. The gene encodes mannosyltransferase I. The gene plays an important role in the normal reproductive development of the *Nilaparvata lugens* (Stål). Inhibition of the function of the gene may reduce the survival rate of the *Nilaparvata lugens* (Stål) and hinder embryonic development. With respect to reduction of the survival rate of the *Nilaparvata lugens* (Stål) and hindering of embryonic development, the present invention can reduce the harm of the *Nilaparvata lugens* (Stål) to rice by killing the *Nilaparvata lugens* (Stål). By using the characteristic that the nucleotide sequence of a highly conserved target gene has no homology with the nucleotide sequence of natural enemies of the *Nilaparvata lugens* (Stål), RNA interference is performed at a nucleic acid level, to avoid the harm to non-target organisms such as natural enemies, thereby realizing green control of the *Nilaparvata lugens* (Stål) while controlling pests.

1 Claim, 3 Drawing Sheets

Specification includes a Sequence Listing.

| Primers | primer sequence (5'-3') | Purpose |
| --- | --- | --- |
| PIGM-F | GGAAGAACAGTCCTGAGTGGC (SEQ ID NO.2) | PCR of PIGM |
| PIGM-R | GAGTTTAATTCGACTAACACAGCAA (SEQ ID NO.3) | |
| qPIGM-F | TTGGCGAATAGCGGTAAGTC (SEQ ID NO.4) | qPCR of PIGM |
| qPIGM-R | GCTGCGAAACTTGGAACACG (SEQ ID NO.5) | |
| q18S-F | GTAACCCGCTGAACCTCC (SEQ ID NO.6) | qPCR of 18S |
| q18S-R | GTCCGAAGACCTCACTAAATCA (SEQ ID NO.7) | |
| dsPIGM-F | GGATCCTAATACGACTCACTATAGCATCATCACACGAGAAACAAGA (SEQ ID NO.8) | Amplify DNA template for synthesizing dsPIGM |
| dsPIGM-R | GGATCCTAATACGACTCACTATAGGCAACGCTGATTCACTGTC (SEQ ID NO.9) | |
| dsGFP-F | GGATCCTAATACGACTCACTATAGGGATACGTGCAGGAGAGGAC (SEQ ID NO.10) | Amplify DNA template for synthesizing dsGFP |
| dsGFP-R | GGATCCTAATACGACTCACTATAGGGCAGATTGTGTGGACAGG (SEQ ID NO.11) | |

FIG. 6

SEQUENCE LISTING

<160> NUMBER OF SEQ ID NOS: 11

<210> SEQ ID NO 1
<211> LENGTH: 1203
<212> TYPE: DNA
<213> ORGANISM: Artificial Sequence
<220> FEATURE:
<223> OTHER INFORMATION: Nilaparvata lugens

<400> SEQUENCE: 1

```
atggtgacct tcagtcaaca ttgtttgatt ggtttaattg taagactttt ttcaatatca    60
ttgggaaaca ttctggatgt gtttacagag gtaaaataca ctgatattga ttacactgta   120
ttctcagatg ctgcaagtca tgtgctgaaa ggcaattcac cattcgatag accgacttac   180
cgctattcgc caatccttgc atatctttta acgccaaaca taatcttgca tcagacttgg   240
ggcaaagttt tgttctcgat cggcgatatt attgtctgta tattgatcag aaacattcta   300
agaagtgaga aaattaatga aaggttatt atgaaatgta tattcttttg gctgtacaat   360
ccgatctcag tgatcatatc taccagaggc aacgctgatt cactgtcagc tatattagtt   420
ctaggaacat tagcagcaat gaaaaataga aattatttaa tggcgggcgt tctgcatgga   480
ctgtctatac atttcaggat ttatcctctg gtctatagtt tggcattgta cttgtcaata   540
tcgccatcca ttgagattgt caaaactgat catttattta aagattaac aaaggctctg   600
aaccccagca tcgaacgact ccgtttggta tcaacgtgct tagtgacgtt gacaacattg   660
acatcaatat ttcattcact ttatggctac aagtttctcc atgaatcgtt tctttaccat   720
ttttcaagac aagatattag acacaacttc tcaatattct tctatttgca gtatctttct   780
gccgatgagc caatttctct tgtttctcgt gtgatgatgc ttcttcctca attacttgtt   840
ttacttgcca tttcaattgt attcggctct gaaaaacaca tatgctttgc tgaattgtgc   900
ctgacagttg taatggtaac tttcaattct gtcttgacat gccagtactt tgtttggttc   960
ttctgcttga ttccgctagc tctgccttat ctgaagttca caaatcttga gtatataata  1020
atcgggttct tatggccagc agctcaactt agttggctct ttccggccta tcttttagag  1080
tttcgaggcc gcaatacttt cattcacata tttttccaaa gcattgcatt ttttgcagca  1140
aatatagtcg tatttactag acttatttgg ggttacaaaa aatcctataa aatcgagagc  1200
tag                                                                 1203
```

<210> SEQ ID NO 2
<211> LENGTH: 21
<212> TYPE: DNA
<213> ORGANISM: Artificial Sequence
<220> FEATURE:
<223> OTHER INFORMATION: PIGM-F primer

<400> SEQUENCE: 2

```
ggaagaacag tcctgagtgg c                                              21
```

<210> SEQ ID NO 3
<211> LENGTH: 25
<212> TYPE: DNA
<213> ORGANISM: Artificial Sequence
<220> FEATURE:
<223> OTHER INFORMATION: PIGM-R primer

<400> SEQUENCE: 3

```
gagtttaatt cgactaacac agcaa                                          25
```

```
<210> SEQ ID NO 4
<211> LENGTH: 20
<212> TYPE: DNA
<213> ORGANISM: Artificial Sequence
<220> FEATURE:
<223> OTHER INFORMATION: qPIGM-F primer

<400> SEQUENCE: 4
ttggcgaata gcggtaagtc                                              20

<210> SEQ ID NO 5
<211> LENGTH: 20
<212> TYPE: DNA
<213> ORGANISM: Artificial Sequence
<220> FEATURE:
<223> OTHER INFORMATION: qPIGM-R primer

<400> SEQUENCE: 5
gctgcgaaac ttggaacacg                                              20

<210> SEQ ID NO 6
<211> LENGTH: 18
<212> TYPE: DNA
<213> ORGANISM: Artificial Sequence
<220> FEATURE:
<223> OTHER INFORMATION: q18S-F primer

<400> SEQUENCE: 6
gtaacccgct gaacctcc                                                18

<210> SEQ ID NO 7
<211> LENGTH: 22
<212> TYPE: DNA
<213> ORGANISM: Artificial Sequence
<220> FEATURE:
<223> OTHER INFORMATION: q18S-R primer

<400> SEQUENCE: 7
gtccgaagac ctcactaaat ca                                           22

<210> SEQ ID NO 8
<211> LENGTH: 46
<212> TYPE: DNA
<213> ORGANISM: Artificial Sequence
<220> FEATURE:
<223> OTHER INFORMATION: dsPIGM-F primer

<400> SEQUENCE: 8
ggatcctaat acgactcact atagcatcat cacacgagaa acaaga                 46

<210> SEQ ID NO 9
<211> LENGTH: 43
<212> TYPE: DNA
<213> ORGANISM: Artificial Sequence
<220> FEATURE:
<223> OTHER INFORMATION: dsPIGM-R primer

<400> SEQUENCE: 9
ggatcctaat acgactcact ataggcaacg ctgattcact gtc                    43

<210> SEQ ID NO 10
<211> LENGTH: 44
<212> TYPE: DNA
<213> ORGANISM: Artificial Sequence
<220> FEATURE:
<223> OTHER INFORMATION: dsGFP-F primer
```

```
<400> SEQUENCE: 10
ggatcctaat acgactcact atagggatac gtgcaggaga ggac        44

<210> SEQ ID NO 11
<211> LENGTH: 43
<212> TYPE: DNA
<213> ORGANISM: Artificial Sequence
<220> FEATURE:
<223> OTHER INFORMATION: dsGFP-R primer

<400> SEQUENCE: 11
ggatcctaat acgactcact atagggcaga ttgtgtggac agg         43
```

PIGM GENE RELATED TO NILAPARVATA LUGENS (STÅL) REPRODUCTION AND APPLICATION THEREOF

REFERENCE TO SEQUENCE LISTING

The substitute sequence listing is submitted as an ASCII formatted text filed via EFS-Web, with a file name of "Substitute_Sequence_Listing_GLP-US-SJDL151.TXT", a creation date of May 3, 2023, and a size of 3903 bytes. The substitute sequence Listing filed via EFS-Web is a part of the specification and is incorporated in its entirety by reference herein.

TECHNICAL FIELD

The present invention belongs to the technical field of PIGM genes related to *Nilaparvata lugens* (Stål) reproduction, in particular to a PIGM gene related to *Nilaparvata lugens* (Stål) reproduction and an application thereof.

BACKGROUND

*Nilaparvata lugens* (Stål) is an insect that feeds on rice phloem juice and damages rice. *Nilaparvata lugens* (Stål) has the characteristics of seasonality, migration and explosiveness and is one of the most important agricultural pests in the Yangtze River valley and Southeast Asia of China.

At present, in agricultural production, chemical control is still the main method for controlling *Nilaparvata lugens* (Stål) due to the characteristics of convenience and rapidness, but chemical control is easy to cause the problems of increase of drug resistance of the pests, residues of harmful substances and vicious circle of explosiveness of high drug resistant pests. In recent years, after some conventional pesticides, such as buprofezin, thiamethoxam and imidacloprid, used to control *Nilaparvata lugens* (Stål), have been suspended, there is a lack of a high-efficiency pesticide that can be continuously used for controlling *Nilaparvata lugens* (Stål) in agricultural production. Although the development of drug resistance and the mechanisms of detoxification and metabolism of *Nilaparvata lugens* (Stål) are still unclear, it is possible to control the *Nilaparvata lugens* (Stål) by molecular biological techniques. Therefore, screening and discovering genes that play an important role in reproduction and development of *Nilaparvata lugens* (Stål) to become targets for controlling *Nilaparvata lugens* (Stål) have important practical significance for the green control strategy of *Nilaparvata lugens* (Stål).

SUMMARY

In order to solve the problems proposed in the above background, the present invention provides a PIGM gene related to *Nilaparvata lugens* (Stål) reproduction and an application thereof. According to the characteristic of high conservation of protein encoded by the PIGM gene, the present invention conducts RNA interference on the target gene, inhibits PIGM expression on *Nilaparvata lugens* (Stål) at the nucleic acid level, significantly reduces the survival rate of the *Nilaparvata lugens* (Stål), and hinders embryonic development.

To achieve the above purpose, the present invention provides the following technical solution: a nucleotide sequence is shown in SEQ ID NO:1; the gene encodes mannosyltransferase I; the gene plays an important role in the normal reproductive development of the *Nilaparvata lugens* (Stål); and inhibition of the function of the gene reduces the survival rate of the *Nilaparvata lugens* (Stål) and hinders embryonic development.

An application of an RNA interference technology of the PIGM gene related to the *Nilaparvata lugens* (Stål) reproduction in control of *Nilaparvata lugens* (Stål) is provided, wherein the RNA interference technology may lead to reduction of the survival rate of the *Nilaparvata lugens* (Stål) and hindering of embryonic development.

Preferably, the application is used for the development of a biological pesticide of the *Nilaparvata lugens* (Stål) and biological control of the *Nilaparvata lugens* (Stål).

Compared with the prior art, the present invention has the following beneficial effects:

With respect to reduction of the survival rate of the *Nilaparvata lugens* (Stål) and hindering of embryonic development, the present invention can reduce the harm of the *Nilaparvata lugens* (Stål) to rice by killing the *Nilaparvata lugens* (Stål).

By using the characteristic that the nucleotide sequence of a highly conserved target gene has no homology with the nucleotide sequence of natural enemies of the *Nilaparvata lugens* (Stål), RNA interference is performed at a nucleic acid level, to avoid the harm to non-target organisms such as natural enemies, thereby realizing green control of the *Nilaparvata lugens* (Stål) while controlling pests.

DESCRIPTION OF THE DRAWINGS

The drawings are used to provide further understanding for the present invention and constitute part of the description. The drawings are used to explain the present invention together with the embodiments of the present invention, and do not constitute a limitation to the present invention. In the drawings:

FIG. 6 shows primers used for PIGM gene cloning, quantitative analysis and dsRNA synthesis.

DETAILED DESCRIPTION

Figure 1:
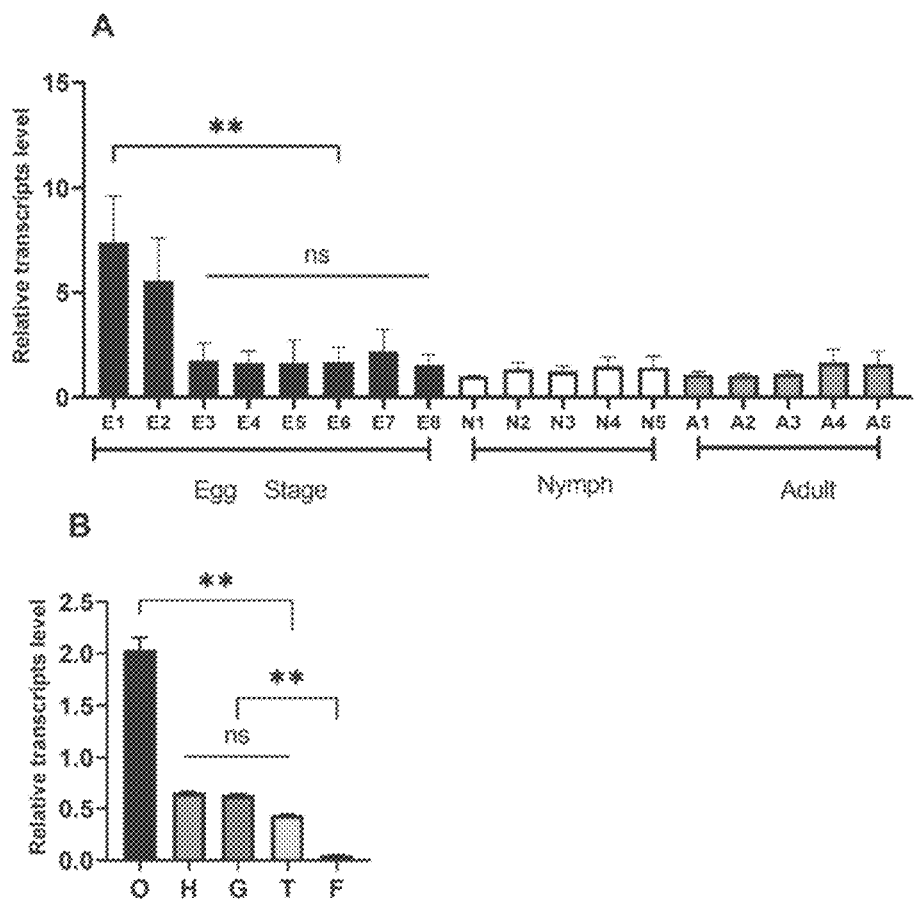
FIG. 1 shows the mRNA expression level of PIGM gene of *Nilaparvata lugens* (Stål)

The technical solution in the embodiments of the present invention will be clearly and fully described below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

EMBODIMENT 1

Referring to FIGS. 1-6, the present invention provides the following technical solution which comprises material and method, as well as results and analysis:

I. Material and Analysis (I) Test *Nilaparvata lugens* (Stål)

Test *Nilaparvata lugens* (Stål) population is a population raised on the susceptible rice variety Taichung Native 1 (TN1), which has been continuously raised on TN1 for more than 50 generations by this laboratory at a raising temperature of 27±1° C., a relative humidity of 60%±5%, and a light period of L: D=16 h: 8 h.

(II) Main Reagents

TaKaRa MiniBEST Universal RNA Extraction Kit, TaKaRa MiniBEST Agarose Gel DNA Extraction Kit, PrimeScript RT reagent Kit With gDNA Eraser, DNA 2000 Marker, SYBR Primix Ex Taq™ II(Tli RNaseH Plus), which are purposed from Dalian TaKaRa Company; MEGAscript™ T7 High Yield Transcription Kit, purposed from Thermo Fisher Scienctific Company, USA. Sequencing and primer synthesis are completed by Sangon Biotech (Shanghai) Co., Ltd.

(III) Cloning of Full-Length cDNA of PIGM Gene of Mannosyltransferase I of *Nilaparvata lugens* (Stål)

*Nilaparvata lugens* (Stål) adults of different ages raised in TN1 rice seedbeds are collected. Total RNA is extracted using TaKaRa MiniBEST Universal RNA Extraction Kit. The Description can be referred to for specific steps. The integrity and purity of the RNA are detected by using agarose gel electrophoresis and Nanodrop2000 (Thermo). By taking 1 μg of total RNA as a template, reverse transcription is conducted by using a PrimeScript RT reagent Kit With gDNA Eraser to synthesize cDNA, and the cDNA is stored at −20° C. for later use.

PCR primers PIGM-F and PIGM-R of PIGM are designed by using primer premier 5.0, and sent to Sangon Biotech (Shanghai) Co., Ltd. for synthesis. Then, by taking reverse-transcribed cDNA as the template, a PCR amplification system is constructed according to the instruction.

The reaction procedure is as follows: at 94° C. for 3 min; at 94° C. for 30 s; at 57° C. for 30 s; at 72° C. for 90 s; 30 cycles; at 72° C. for 10 min; storage at 4° C.

After the reaction is completed, the PCR product is subjected to 1% agarose gel electrophoresis to verify the band size and amplification efficiency.

Subsequently, the amplified DNA fragments are gelled and recovered according to the instruction of the TaKaRa MiniBEST Agarose Gel DNA Extraction Kit Ver. 4.0.

The recovered DNA fragments are ligated with pMD19-T vector overnight at 16° C.; the ligated product is transformed into JM109 competent *Escherichia coli* by a heat shock method; the bacterial solution is coated on Amp-resistant LB medium; single colonies are randomly selected the next day; and the bacterial solution is verified by PCR and then sent to Sangon Biotech (Shanghai) Co., Ltd. for sequencing.

After sequencing results are correct by comparison, the plasmid is extracted according to the instructions of SanPrep column plasmid DNA small-volume extraction kit, and the extracted plasmid is named pMD19-T-PIGM and stored at −20° C. for later use.

(IV) Analysis of the Expression Pattern of *Nilaparvata lugens* (Stål) PIGM Gene Designed qPIGM-F and qPIGM-R are used as fluorescence quantitative PCR primers of the PIGM gene. 18S rRNA is used as a reference gene (as shown in FIG. 6), and designed q18S—F and q18S—R are used as fluorescence quantitative PCR primers of the 18S rRNA.

The relative expression levels of PIGM in different instars of *Nilaparvata lugens* (Stål) are detected by the fluorescence quantitative PCR technology, including 1-8 days of developing eggs, 1-5 instars of nymphs and 1-5 days of developing female adults.

The fluorescence quantitative PCR procedure is: at 94° C. for 30 s; at 94° C. for 5 s; at 60° C. for 30 s, with 40 cycles.

(V) RNA Interference

PIGM double-stranded RNA (dsPIGM) is used for injection interference, and GFP double-stranded RNA (dsGFP) is used as control.

PCR primers for dsPIGM synthesis of the DNA template are designed by using primer premier 5.0; T7 promoter sequence (TAATACGACTCACTATA) is added to the 5' ends of the designed primers; then, six protective bases (GGATCC) are added to the 5' ends of the promoter sequence; and the designed dsPIGM primers are dsPIGM-F and dsPIGM-R respectively.

Similarly, PCR primers for dsPIGM synthesis of the DNA template for dsGFP are designed, which are dsGFP-F and dsGFP-R respectively (as shown in FIG. 6).

The primers are sent to Sangon Biotech (Shanghai) Co., Ltd. for synthesis. dsPIGM and dsGFP are synthesized respectively according to the instructions of MEGAscript™ T7 High Yield Transcription Kit.

*Nilaparvata lugens* (Stål) nymphs of the fifth instar are collected, then raised in separate glass bottles in batches, and fed with TN1 rice seedlings. The bottle mouths are covered with gauze and tied tightly with rubber bands. Freshly hatched long-winged female adults are collected in glass bottles every 12 h for injection.

The synthesized dsRNA samples are taken out of a refrigerator at −80° C. and diluted to 5000 ng/μL after freeze-thawed. The collected female *Nilaparvata lugens* (Stål) are placed on ice for 5 min to induce temporary shock.

Under a microscope, 0.05 μl of dsRNA is slowly injected into the abdomen back of the *Nilaparvata lugens* (Stål) with a microinjection needle. After injection, the *Nilaparvata lugens* (Stål) are gently placed in a glass bottle, and after resuscitated (with recovery of motion ability), the *Nilaparvata lugens* (Stål) are transferred into a glass bottle with a TN1 rice seedbed and raised (n=50). The mouth of the glass bottle is covered with gauze and tightened with rubber bands. After all the *Nilaparvata lugens* (Stål) are injected, the *Nilaparvata lugens* (Stål) are transferred into a phytotron, and raised.

The *Nilaparvata lugens* (Stål) injected with dsPIGM is used as an experimental group. Accordingly, dsGFP is used as a control group. Except for the difference of dsRNA, the two groups have the same operation. On the second day after injection, one injected female and two untreated males are paired and fed separately in a 50 mL centrifuge tube with the rice seedbed. The centrifuge tube with the rice seedbed is replaced every day (the rice seedlings are not discarded), and dead *Nilaparvata lugens* (Stål) are removed and counted. A survival rate is calculated.

Five females are collected at day 2, day 3 and day 5 respectively, and total RNA is extracted and subjected to fluorescence quantitative PCR detection. After the nymphs of *Nilaparvata lugens* (Stål) are hatched from the rice seedlings in the centrifugal tube of the control group, all the rice seedlings used for raising the females are cut off, and eggs in the seedlings are taken out and photographed.

(VI) Data Statistics and Analysis

Significant differences are analyzed through SPSS 20.0, and data charts are drawn through GraphPad Prism 8.0.2 software.

II. Results and Analysis (I) Full-Length cDNA Cloning and Sequence Analysis of *Nilaparvata lugens* (Stål) PIGM After the cDNA of *Nilaparvata lugens* (Stål) is used as a template for PCR amplification, a specific band with the expected length of 1500 bp is obtained. It is found through ORF Finder analysis that ORF of PIGM has 1203 nucleotides, encodes 400 amino acids, and has a molecular weight of 46.6 kDa and a predicted isoelectric point of 9.21. PIGM does not contain signal peptide, but contains a structural domain with the activity of PIGM mannosyltransferase. PIGM has 38 phosphorylation modification sites, including 22 serine modification sites, 12 threonine modification sites, 4 tyrosine modification sites, and 2 N-glycosylation modification sites. The comparison results of MEGA X and NCBI Blast show that *Nilaparvata lugens* (Stål) PIGM and *Laodelphax striatellus* have 99.58% homology, and a core structural domain of PIGM between different species is highly conserved.

(II) Analysis of the Expression Pattern of *Nilaparvata lugens* (Stål) PIGM

The fluorescence quantitative PCR detection indicates that PIGM is expressed to different degrees in different instars and different tissues of *Nilaparvata lugens* (Stål).

PIGM is specifically highly expressed at 1-2 days in egg stage, and the expression level at 4-5 days in adults is slightly higher than that at 1-3 days (as shown in FIG. 1, A). The expression level of PIGM is highest in the ovary of the female adult; the expression levels of PIGM are similar in the head, thorax and gut, and barely different; and the expression level of PIGM is lowest in the fat body (as shown in FIG. 1, B).

This suggests that PIGM plays an important role in reproductive development and early embryo of *Nilaparvata lugens* (Stål).

In FIG. 1:

E1-E8: day 1 to day 8 of egg stage;

N1-N5: the first instar to the fifth instar of nymph stage;

A1-A5: female adults from day 1 to day 5 after freshly hatched;

H: head; T: thorax; G: -gut; F: fat body; O: ovary;

*: This indicates significant differences between different samples (one-way analysis of variance and multiple comparison using Tukey method, P<0.05);

The data in the figure is a mean value of 3 replicates±standard deviation.

(III) Effect of RNA interference on the expression level of *Nilaparvata lugens* (Stål) PIGM The results of fluorescence quantitative PCR detection show that the mRNA expression level of the PIGM gene is low in the RNA interference group fed with 5000 ng/μL of dsPIGM. Compared with the dsGFP control group, the expression levels of PIGM in the dsPIGM interference group on day 2, day 3 and day 5 after treatment are decreased by 80%, 85% and 79% respectively compared with the control group, with significant differences (P<0.05). The above results indicate that the RNA interference results of the PIGM gene are effective (as shown in FIG. 2).

Figure 2:
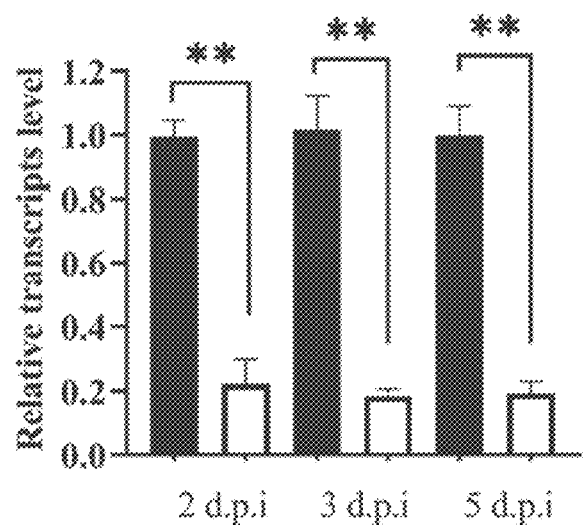
FIG. 2 shows the effect of RNA interference on the expression level of PIGM gene of *Nilaparvata lugens* (Stål)

In FIG. 2:

d.p.i: days post RNA injection;

*: This indicates significant differences between different treat groups (t test, P<0.05);

The data in the figure is a mean value of 3 replicates±standard deviation.

(IV) Effect of RNA Interference of PIGM Gene on Survival Rate of *Nilaparvata lugens* (Stål)

RNA interference to expression of PIGM has a significant effect on the survival rate of *Nilaparvata lugens* (Stål). From day 3, the survival rates between the dsPIGM treatment group and the dsGFP control group have significant differences (P<0.05). On day 8, all the *Nilaparvata lugens* (Stål) in the treatment group die, while 50% of individuals in the control group are still alive, and the longest survival period of *Nilaparvata lugens* (Stål) in the control group is 15 days (as shown in FIG. 3).

Therefore, the interference of PIGM gene has a great effect on the normal survival of *Nilaparvata lugens* (Stål), and PIGM is of great significance for the survival of *Nilaparvata lugens* (Stål).

Figure 3:
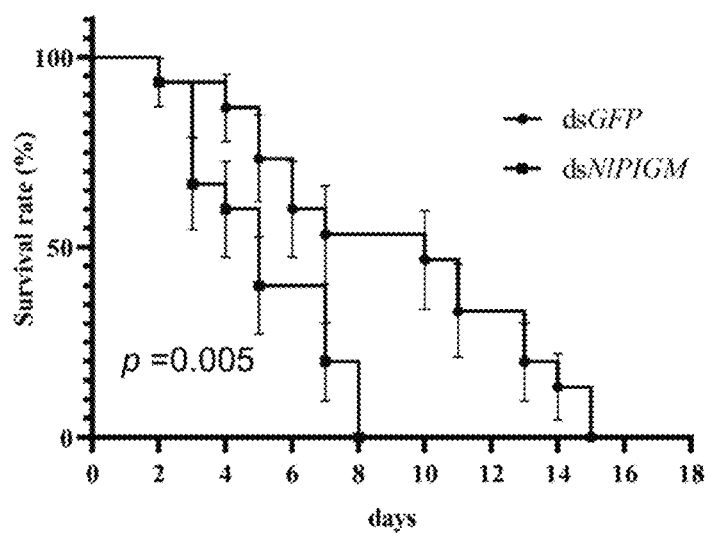
FIG. 3 shows the effect of RNA interference of PIGM gene on survival rate of *Nilaparvata lugens* (Stål)

In FIG. 3: the significant differences in the data are analyzed through Mantel-Cox test in GraphPad Prism 8.0.2 software.

(V) Effect of RNA Interference of PIGM Gene on Ovarian Development of *Nilaparvata lugens* (Stål).

The RNA interference of PIGM has an effect on the ovary of *Nilaparvata lugens* (Stål). Compared with the dsGFP control group, the ovarian development of the females in the dsPIGM treatment group is significantly delayed. After 5 days from the injection of dsRNA, a large number of mature banana-shaped eggs are produced in the ovary of the dsGFP control group, but the ovary in the dsPIGM treatment group hardly has any eggs (as shown in FIG. 4).

Figure 4:
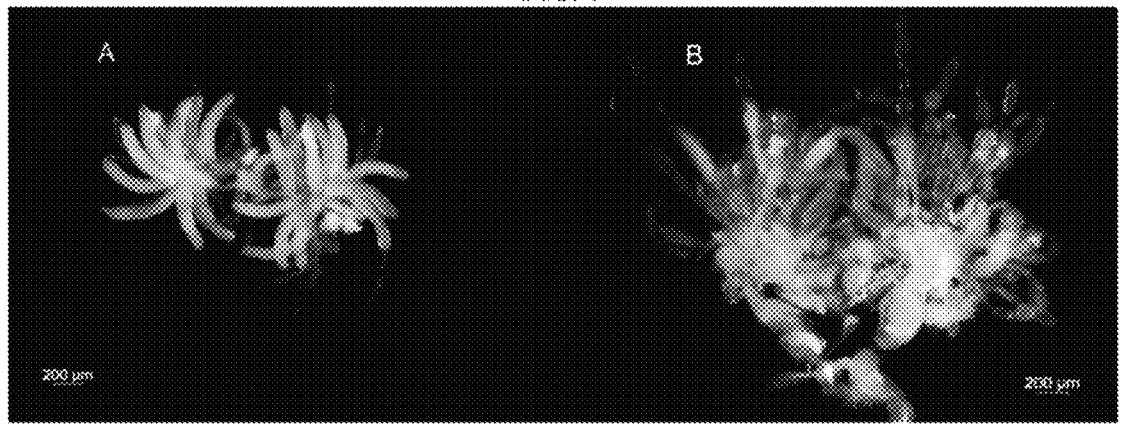
FIG. 4 shows the effect of RNA interference of PIGM gene on ovarian development of *Nilaparvata lugens* (Stål)

In FIG. 4:

(A) After 5 days from the injection of dsGFP, the development of the ovary of *Nilaparvata lugens* (Stål) female is normal;

(B) After 5 days from the injection of dsPIGM, the development of the ovary of *Nilaparvata lugens* (Stål) female is delayed.

(VI) Effect of Interference of PIGM Gene on Embryonic Development of *Nilaparvata lugens* (Stål).

Figure 5:
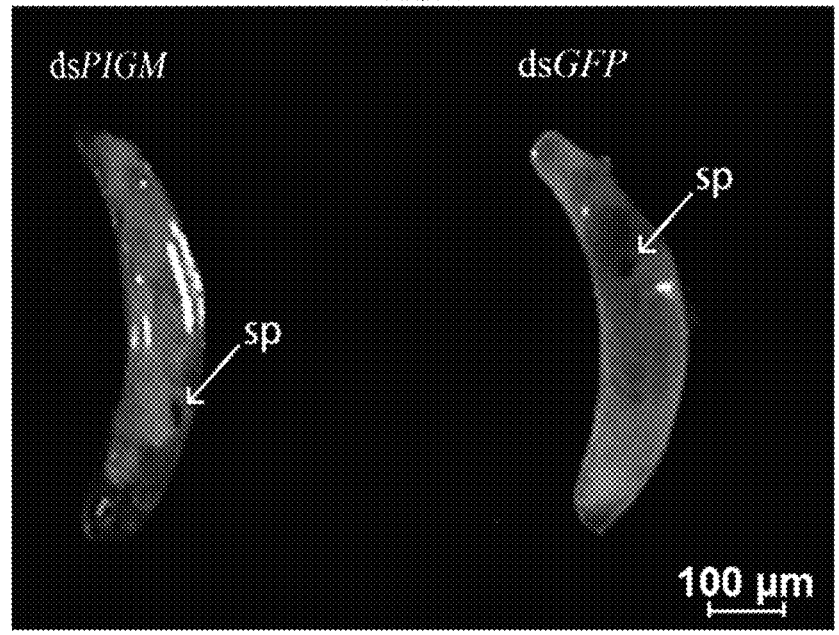
FIG. 5 shows the effect of RNA interference of PIGM gene on egg development of *Nilaparvata lugens* (Stål) at day 5.

Eggs produced by the females of the dsPIGM treatment group and the dsGFP control group begin to generate eye spots on day 5. Although the colors of the eye spots are darker with the development of the eggs, the eye spots of the eggs injected with dsPIGM appear at the "posterior pole" of the eggs and remain at the "posterior pole" until day 7. The eggs cannot hatch and eventually fester in the rice seedlings. The eye spots of the eggs produced by *Nilaparvata lugens* (Stål) injected with dsGFP appear at the "anterior pole" of the eggs, and the eggs can hatch normally (as shown in FIG. 5). This indicates that the RNA interference of PIGM makes embryos of *Nilaparvata lugens* (Stål) fail to normally develop.

In FIG. 5: sp: eye spot.

Finally, it should be noted that the above description is only a preferred embodiment of the present invention, and is not intended to limit the present invention. Although the present invention is described in detail with reference to the above embodiment, those skilled in the art may still modify the technical solution recorded in the above embodiment, or equivalently replace some of the technical features. Any modification, equivalent replacement, improvement, etc. made within the spirit and the principle of the present invention shall be included within the protection scope of the present invention.

The invention claimed is:

1. A method for reducing a survival rate of *Nilaparvata lugens* (Stål), comprising:

injecting 0.05 μl of PIGM double-stranded RNA (dsPIGM) into the *Nilaparvata lugens* (Stål) for interference; the PIGM gene having a nucleotide sequence shown in SEQ ID NO.1; and inhibiting the gene encoding mannosyltransferase I.

* * * * *